(12) United States Patent
Lee et al.

(10) Patent No.: US 8,080,262 B2
(45) Date of Patent: Dec. 20, 2011

(54) ENCAPSULATED PEPTIDE AMPHIPHILE NANOSTRUCTURES

(75) Inventors: Hyung-Kun Lee, Jeonju (KR); Stephen Soukasene, Evanston, IL (US); Samuel I. Stupp, Chicago, IL (US)

(73) Assignee: Northwestern University, Evanston, IL (US)

( * ) Notice: Subject to any disclaimer, the term of this patent is extended or adjusted under 35 U.S.C. 154(b) by 867 days.

(21) Appl. No.: 11/923,428

(22) Filed: Oct. 24, 2007

(65) Prior Publication Data
US 2010/0172961 A1 Jul. 8, 2010

Related U.S. Application Data

(60) Provisional application No. 60/854,045, filed on Oct. 24, 2006.

(51) Int. Cl.
*A61K 9/127* (2006.01)
*A61K 38/00* (2006.01)
*A61K 38/08* (2006.01)

(52) U.S. Cl. .................. 424/450; 514/1.1; 514/21.6
(58) Field of Classification Search .................. None
See application file for complete search history.

(56) References Cited

U.S. PATENT DOCUMENTS

| | | | |
|---|---|---|---|
| 5,662,930 A * | 9/1997 | Ahl et al. ............... | 424/450 |
| 6,096,863 A | 8/2000 | Fields et al. | |
| 6,680,215 B2 | 1/2004 | Stupp et al. | |
| 6,890,654 B2 | 5/2005 | Stupp et al. | |
| 2004/0001893 A1 | 1/2004 | Stupp et al. | |
| 2004/0018961 A1 | 1/2004 | Stupp et al. | |
| 2005/0118678 A1 | 6/2005 | Mayo | |

OTHER PUBLICATIONS

Lee, Hsien-Ming Purdue University Graduate School, Thesis Acceptance obtained from: Dissertation Abstracts International, 2004. Title: Liposomal cargo unloading induced by pH sensitive peptides and probing peptide self-replication within liposomes. 151 pages.*
Ruysschaert et al. Liposome-Based Nanocapsules. IEE Transactions on Nanobioscience. Mar. 2004, vol. 3, Nol. 1, pp. 49-55.*
Liang et al. Encapsulation of lipopeptides within liposomes: Effect of number of lipid chains, chain length, and method of liposome preparation. International Journal of Pharmaceuticals. 2005. vol. 301, pp. 247-254.*
Chen et al. Lipid Encapsulation of Arsenic Trioxide Attenuates Cytotoxicity and Allows for Controlled Anticancer Drug Release. Chen et al. JACS Communications. Sep. 26, 2006, vol. 128, pp. 13348-13349.*
Johansson, 2008, "Light activated functional mesostructure silica," J Sol Gel Sci Technol, pp. 313-322, vol. 46.
Allen and Cullis, 2004, "Drug Delivery Systems: Entering the Mainstream," Science, 303:1818-1822.
Ulrich, 2002, "Biological Aspects of Using Liposomes as Delivery Vehicles," Biosci. Rep. 22:129-50.
Hartgerink et al., 2002, "Peptide-amphiphile nanofibers: A versatile scaffold for the preparation of self-assembling materials," Proc. Natl. Acad. Sci. 99:5133-38.
Hartgerink et al., 2001, Self-Assembly and Mineralization of Peptide-Amphiphile Nanofibers Science 294:1684-88.
Silva et al., 2004,"Selective Differentiation of Neural Progenitor Cells by High-Epitope Density Nanofibers," Science 303: 1352-55.
Beniash et al., 2005, "Self-assembling peptide amphiphile nanofiber matrices for cell entrapment," Acta Bio. 1:387-97.
Bull et al., 2005, "Self-Assembled Peptide Amphiphile Nanofibers Conjugated to MRI Contrast Agents,"Nano Lett. 5:1-4.
International Search Report and Written Opinion, PCT/US2007/082417, dated Jun. 20, 2008.
Gregoriadis et al., 1999, "Vaccine Entrapment in Liposomes," Methods 19:156-162.
Shi and Pardridge, 2000, "Noninvasive gene targeting to the brain," Proc. Natl. Acad. Sci. 97:7567-7572.
Monnard et al., 1997, "Entrapment of Nucleic Acids in Liposomes," Biochim. Biophys. Acta 1329:39-50.
Cortese et al., 1989, "Actin polymerization induces a shape change in actin-containing vehicles," Proc. Natl. Acad. Sci. 86:5773-77.
Miyata et al., 1992, "Morphological changes in liposomes caused by polymerization of encapsulated actin and spontaneous formation of actin bundles," Proc. Natl. Acad. Sci. 89:11547-51.
Palmer et al., 2003, "Atomic Force Microscopy and Light Scattering of Small Unilamellar Actin-Containing Liposomes," Biophys. 1. 85:1233-1247.
Li and Palmer, 2004, "Effect of Actin Concentration on the Structure of Actin-Containing Liposomes," Langmuir 20:4629-4639las.
Lasic, 1996, "Doxorubicin in sterically stabilized liposomes," Nature, 380:561-566.
Li et al., 1998, "Doxorubicin physical state in solution and inside liposomes loaded via a pH gradient," Biochem. Biophys. Acta 1415:23-40.
Abraham et al., 2002, "Formation of transition metal—doxorubicin complexes inside liposomes," Biochim. Piophys. Acta 1565:41-54.
Niece et al., 2003, "Self-Assembly Combining Two Bioactive Peptide-Amphiphile Molecules into Nanofibers by Electrostatic Attraction," J. Am. Chem. Soc. 125:7146-7147.
Stendahl et al., 2006, "Intermolecular Forces in the Self-Assembly of Peptide Amphiphile Nanofibers," Adv. Func. Mat. 16:499-508.
Shirai and Tsunooka, 1996, "Photacid and Photobase Generators: Chemistry and Applications to Polymeric Materials," Prog. Polym Sci. 21:1-45.
Crivello et al., 1999, "The Discovery and Development of Onium Salt Cationic Photoinitiators," J. Polym. Sci. Part A. Polym. Chem. 37:4241-4254.

(Continued)

*Primary Examiner* — Marcela M Cordero Garcia
(74) *Attorney, Agent, or Firm* — Casimir Jones, S.C.

(57) ABSTRACT

The present invention provides compositions and methods for creating encapsulated peptide amphiphilic nanostructures useful in treating diseases. In particular, the present invention provides compositions and methods for preparing peptide amphiphile nanostructures that are encapsulated in liposomes by the application of light, and using such compositions in treating diseases, such as cancer.

23 Claims, 6 Drawing Sheets

OTHER PUBLICATIONS

MacDonald et al., 1994, "Chemical Amplification in High-Resolution Imaging Systems," Acc. Chern. Res. 27:151-158.

Ayabe et al., 2003, "Binary organogelators which show light and temperature responsiveness," Org. Biomol. Chern. 1:2744-47.

Eastoe and Vesperinas, 2005, "Self-assembly of light-sensitive surfactants," Soft Matter 1:338-347.

Geiger et al., 1999, "Organogels Resulting from Competing Self-Assembly Units in the Gelator: Structure, Dynamics, and Photophysical Behavior of Gels Formed from Cholesterol-Stilbene and Cholesterol-Squaraine Gelators," Langmuir 15:2241-2245.

Ikeda et al., 2003, "Anisotropic Bending and Unbending Behavior of Azobenzene Liquid-Crystalline Gels by Light Exposure," Adv. Mat. 15:201-205.

Kazakov et al., 2003, "Poly(N-isopropylacrylamide-co-1-vinylimidazole) Hydrogel Nanoparticles Prepared and Hydrophobically Modified in Liposome Reactors: Atomic Force Microscopy and Dynamic Light Scattering Study," Langmuir 19:8086-8093.

Murata et al., 1994, "Thermal and Light Control of the Sol-Gel Phase Transition in Cholesterol-Based Organic Gels. Novel Helical Aggregation Modes as Detected by Circular Dichromism and Electron Microscopic Observation," J. Am. Med. Soc. 116:6664-6676.

Nakano et al., 2003, "Photoresponsive Behavior of Azobenzene Liquid-Crystalline Gels," Mol. Cryst. Liq. Cryst. 398:1-9.

Akgun et al., 1981, "Metalation of o-Halostyrene Oxides. Preparation of Benzocyclobutenols," J. Org. Chem. 46:2730-2734.

Sakamizu et al., 1995, "Water-soluble onium salts—A new class of acid generators for chemical amplicfication positive resists," Polym. Mat. Sci. Eng. 72:199-200.

Ruberti et al., 2003, "Quick-Freeze/Deep-Etch Visualization of Age-Related Lipid Accumulation in Bruch's Membrane," Invest. Opthalmol. Vis. Sci. 44: 1753-59.

Martinez et al., 1995, "FTIR Spectroscopy of Alanine-Based Peptides: Assignment of the Amide l' Modes for Random Coil and Helix," J. Struct. Biol. 114:23-27.

Guler et al., 2005, "Encapsulation of pyrene within self-assembled peptide amphiphile nanofibers," J. Mater. Chem. 15:4507-4512.

* cited by examiner

A. 1.0 μM 5-Azacytidine

B. 5-Azacytidine

ENCAPSULATED PEPTIDE AMPHIPHILE NANOSTRUCTURES

This application claims priority to U.S. Provisional Application No. 60/854,045, incorporated herein by reference in its entirety.

This invention was made with government support under Grant No. U54CA119341 awarded by the National Institutes of Health's National Cancer Institute. The government has certain rights in the invention.

FIELD OF THE INVENTION

The present invention provides compositions and methods for creating encapsulated peptide amphiphilic nanostructures useful in treating diseases. In particular, the present invention provides compositions and methods for preparing peptide amphiphile nanostructures that are encapsulated in liposomes by the application of light, and using such compositions in treating diseases, such as cancer.

BACKGROUND OF THE INVENTION

Liposomes are spherical vesicles composed of a closed bilayer membrane that entraps part of the surrounding media. They have been used as biocompatible carriers of drugs, peptides, proteins or DNA for pharmaceutical, cosmetic, and biochemical purposes (Allen and Cullis, 2004, Science 303: 1818; Ulrich, 2002, Biosci. Rep. 22:129). Peptide amphiphiles (PAs) are comprised of aliphatic chains and oligopeptide head groups (Hartgerink et al., 2002, Proc. Natl. Acad. Sci. 99:5133; Hartgerink et al., 2001, Science 294: 1684). Self-assembly of PAs by β-sheet formation of the peptide segments and hydrophobic collapse of the aliphatic chains results in one-dimensional nanofibers or networks thereof to give gels in certain conditions. This PA nanofiber system has shown potential for various applications including regenerative medicine (silva et al., 2004, Science 303:1352), tissue engineering (Beniash et al., 2005, Acta Bio. 1:387) or chemotherapy (Bull et al., 2005, Nano Lett. 5:1) based on the epitopes displayed on the periphery. However, the delivery of therapeutic agents by bare nanostructures would be deleterious to normal tissues, and as such is not a viable alternative for therapeutic treatments like chemotherapy.

As such, what is needed are ways of utilizing emerging technologies such that their therapeutic value is realized.

SUMMARY OF THE INVENTION

The present invention provides compositions and methods for creating encapsulated peptide amphiphilic nanostructures useful in treating diseases. In particular, the present invention provides compositions and methods for preparing peptide amphiphile nanostructures that are encapsulated in liposomes by the application of light, and using such compositions in treating diseases, such as cancer.

In the application of chemotherapy, it is not possible to use PA fibers bearing apoptotic peptide sequences in the form of bare nanostructures given the potentially destructive effect on normal cells. However, it is contemplated that if encapsulated into liposomes having targeting moieties, these PAs could be used as efficient chemotherapy reagents by minimizing effects toward normal cells as demonstrated by previous studies on encapsulation of DNA, protein and drug into liposomes (Lasic, 1997, Lipsomes in gene delivery, CRC Press, Boca Raton, Fla.; Gregoriadis et al., 1999, Methods 19:156; Shi and Pardridge, 2000, Proc. Natl. Acad. Sci. 97:7567; Monnard et al., 1997, Biochim. Biophys. Acta 1329:39). Examples demonstrating formation of one-dimensional objects in the liposome interior include the use of actin fibers (Cortese et al., 1989, Proc. Natl. Acad. Sci. 86:5773; Miyata et al., 1992, Proc. Natl. Acad. Sci. 89:11547; Palmer et al., 2003, Biophys. J. 85:1233; Li and Palmer, 2004, Langmuir 20:4629) or doxorubicin fibril precipitates (Lasic, 1996, Nature, 380:561; Li et al., 1998, Biochem. Biophys. Acta 1415:23; Abraham et al., 2002, Biochim. Piophys. Acta 1565: 41) with formation induced by ion injection or pH gradients that depend on the diffusion phenomena through liposomal membranes.

The present application provides compositions and methods for the triggered self-assembly of PA nanofibers inside liposomes, for example, by light irradiation leading to highly dense bundles of one-dimensional objects packed in a confined space. Self-assembly of PAs can be controlled by pH, electrostatic interaction, and addition of multivalent ions, causing the ionic character of certain amino acid side chains to be screened so that PAs can effectively interact with each other through hydrogen bonding and induced hydrophobic collapse (Hartgerink et al., 2002; Hartgerink et al., 2001; Niece et al., 2003, J. Am. Chem. Soc. 125:7146; Stendahl et al., 2006, Adv. Func. Mat. 16:499). The present invention also provides compositions made using such approaches and provides for use of those compositions. To assemble PA nanofiber structures inside liposomes, in some embodiments, it is described herein the use of photoacid generators (PAGs) or photobase generators (PBGs) to control the pH of the aqueous compartment inside the liposomes. Photoacid generators are compounds widely used in the lithographic patterning of semiconductors (Shirai and Tsunooka, 1996, Prog. Polym Sci. 21:1; Crivello et al., 1999, J. Polym. Sci. Part A. Polym. Chem. 37:4241; MacDonald et al., 1994, Acc. Chem. Res. 27:151). This class of compounds generates acidic conditions when irradiated with light. Photobase generators are known to generate basic conditions when irradiated with light. The present invention is not limited to a particular mechanism. Indeed, an understanding of the mechanism is not necessary to practice the present invention. Nonetheless, it is contemplated that, for negatively charged PAs, lowering the pH of the aqueous compartment of the liposome by irradiation of encapsulated PAG triggers the self-assembly of PAs into nanofibers inside the liposome. Conversely, for positively charged PAs, increasing the pH of the aqueous compartment of the liposome by irradiation of encapsulated PBG triggers the self-assembly of PAs into nanofibers inside the liposome. There are many examples of structures triggered by light, for example, light sensitive gel or liquid crystals (Ayabe et al., 2003, Org. Biomol. Chem. 1:2744; Eastoe and Vesperinas, 2005, Soft Matter 1:338, Geiger et al., 1999, Langmuir 15:2241; Ikeda et al., 2003, Adv. Mat. 15:201; Kazakov et al., 2003, Langmuir 19:8086; Murata et al., 1994, J. Am. Med. Soc. 116:6664; Nakano et al., 2003, Mol. Cryst. Liq. Cryst. 398:1). It is contemplated that nanofiber formation of PAs inside liposomes by irradiation provides a method for creating one self-assembled structure inside another self-assembled structure, thereby providing useful methods and compositions for targeted drug therapy.

In some embodiments, the present invention provides methods for creating liposome encapsulated peptide amphiphiles comprising liposomes, peptide amphiphiles, and photoacid or photobase generators such that exposing the compositions to light triggers the creation of the liposome encapsulated peptide amphiphiles. In some embodiments, the peptide amphiphiles are taken from a group consisting of PA 1, PA 2 and PA 3. In some embodiments, the photoacid generator is benzyldimethylsulfonium chloride. In some embodiments, the present invention provides for methods of using the liposome encapsulated peptide amphiphiles in treating and/or studying a disease in a subject.

In some embodiments, the present invention provides compositions, pharmaceutically acceptable or otherwise, comprising liposomes, peptide amphiphiles, and a photoacid or photobase generator. In some embodiments, the components of the compositions of the present invention are provided a user is a kit format, such that the user can make and/or use a liposome encapsulated peptide amphiphile as described herein. In some embodiments, these compositions are created using the methods as described herein for use in vitro (e.g., in cell culture) or in vivo (e.g., in a subject) for diagnostic, research, or therapeutic applications.

DEFINITIONS

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer or is being screened for a cancer. A subject suspected of having cancer may also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental exposure, previous incidents of cancer, preexisting non-cancer diseases, and lifestyle.

As used herein, the term "cancer marker genes" refers to a gene or gene fusion whose expression level, alone or in combination with other genes, is correlated with cancer or prognosis of cancer. The correlation may relate to either an increased or decreased expression of the gene. For example, the expression of the gene may be indicative of cancer, or lack of expression of the gene may be correlated with poor prognosis in a cancer patient.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

DETAILED DESCRIPTION OF THE INVENTION

The liposome is a self-assembled structure where a lipid bilayer surrounds an aqueous compartment. With a typical volume on the order of one thousandth of a cubic micron, this interior compartment has been used to carry drugs, peptides, proteins and DNA for applications in molecular biology, pharmaceuticals, and cosmetics.

The unique class of peptide amphiphiles (PAs) as described in embodiments herein for incorporation into liposomal delivery systems is comprised of three segments: a linear aliphatic chain, a peptide segment that promotes β-sheet formation, and a peptide epitope which can be modified according to the application. These PA molecules have been previously reported and it is contemplated that any such PAs will be suitable for compositions and methods of the present invention as described herein. In aqueous media, self-assembly of these PA monomers into cylindrical nanofibers can be triggered by a change in pH or salt concentration. Networks of these nanofibers can further form three dimensional gel scaffolds resembling extracellular matrices.

Figure 1:
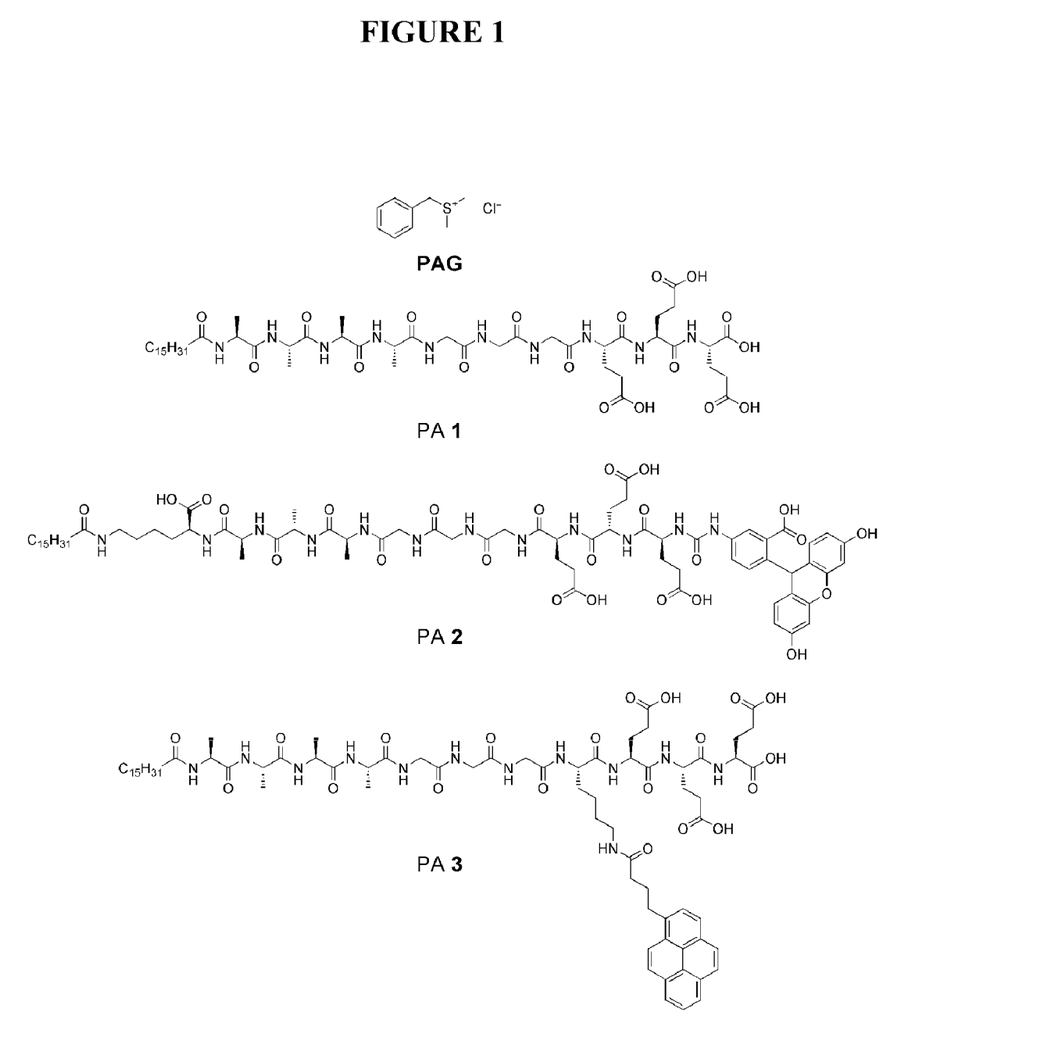
FIG. 1 shows the chemical structures of peptide amphiphiles PA 1, PA 2 and PA 3 and an exemplary photoacid generator (PAG) benzyldimethylsulfonium chloride.
Figure 5:
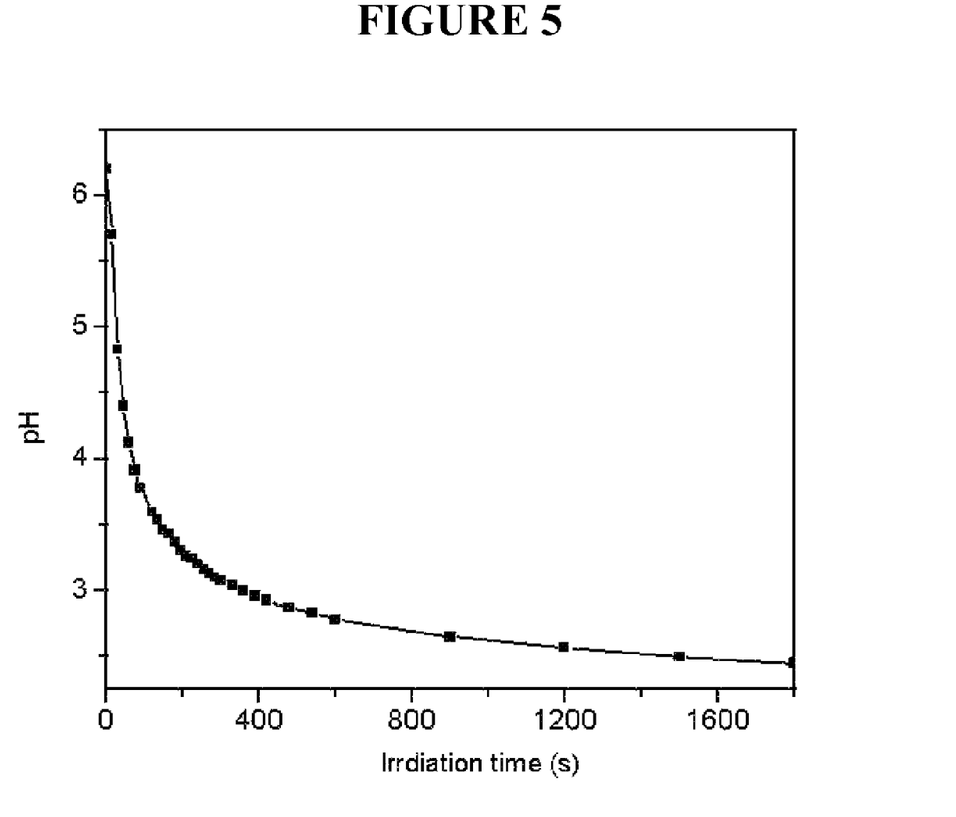
FIG. 5 shows the pH change of a 0.1 wt % PAG solution in water versus irradiation at 254 nm.

In one embodiment, to induce nanofiber formation of PAs inside a liposome, a water soluble PAG, for example, benzyldimethylsulfonium chloride (Akgun et al., 1981, J. Org. Chem. 46:2730; Sakamizu et al., 1995, Polym. Mat. Sci. Eng. 72:199) was introduced inside the liposome with the PA. It is contemplated that photolysis of PAG by ultaviolet (UV) irradiation generates a radical cation, which reacts with solvent to give a protic acid, thereby decreasing the pH inside the liposome (Crivello et al., 1999). In bulk solution, the pH-reducing effect of the photoacid generator is observed as a function of irradiation time, leveling out at pH 2.5 (FIG. 5). A 10 mg/mL solution of PA 1 (FIG. 1) and 4 equivalents of PAG gels after 1 min irradiation with 254 nm light was created. A transmission electronic micrograph (TEM) of the gel revealed a network of nanofibers approximately 10 nm in diameter and several microns in length. Encapsulation of the PA in the aqueous interior of the liposomes was achieved by using a PA solution to hydrate a lipid film by evaporation from an organic solution. The sequestration of the PA was demonstrated by confocal microscopy. PA 1 (FIG. 1) was doped with a green fluorescent-tagged PA 2 (1:100) and introduced as an aqueous solution to a phospholipid film that was doped with a red-fluorescent lipid (Dil-C18, Fluka) (1:1000). Prior to characterization by confocal microscopy, the liposome mixture was treated by size exclusion chromatography to remove unencapsulated PA molecules.

Figure 2:
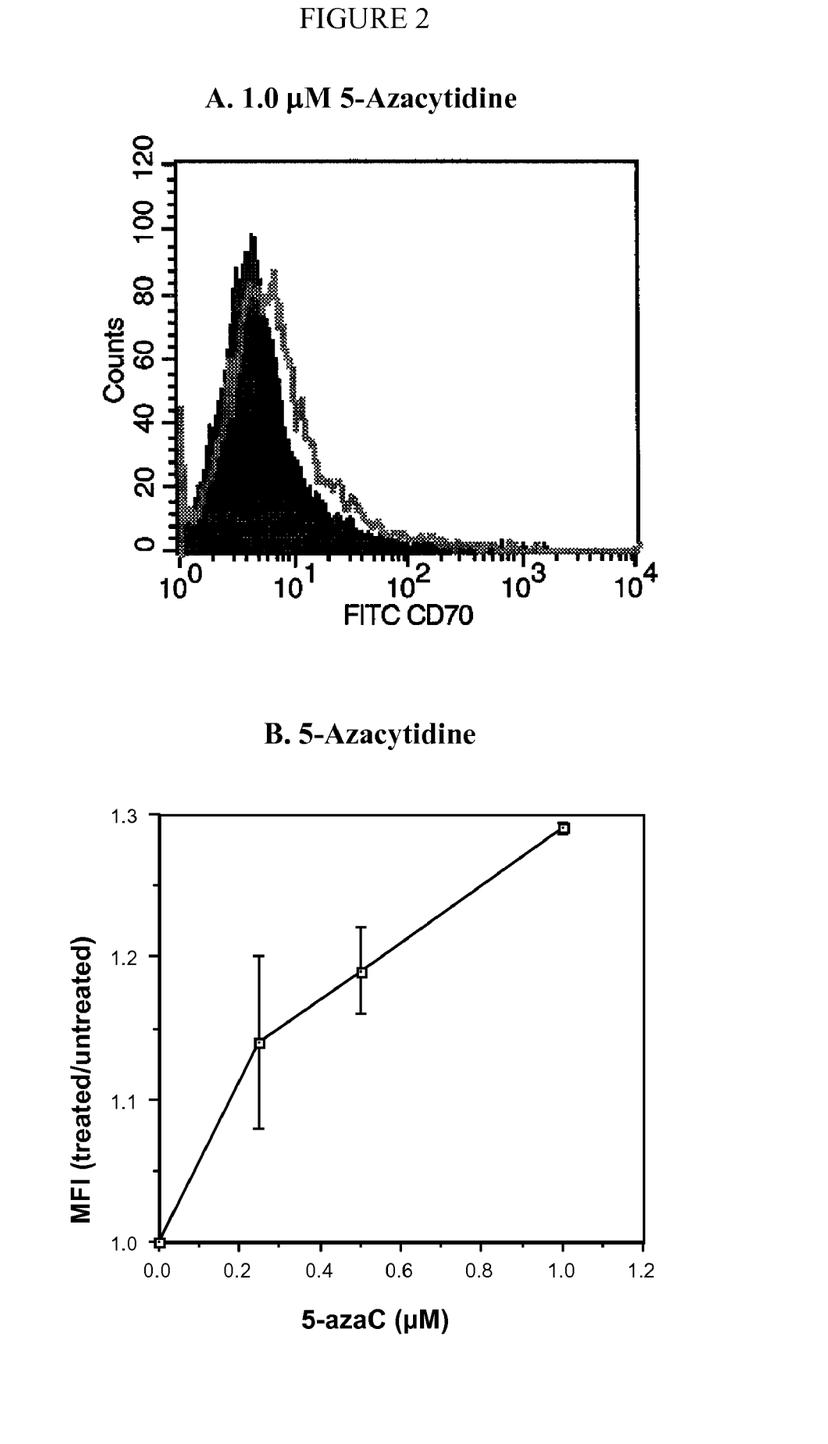
FIG. 2 shows an electron micrograph image of liposomes containing a network of nanofibers.

Further investigation of the PA nanostructure in liposomes was performed using a quick-freeze/deep-etch (QFDE) technique for investigating the inner space of liposomes containing PA 1 (0.5 wt %) and PAG after irradiation (Ruberti et al., 2003, Invest. Opthalmol. Vis. Sci. 44:1753). The inner space of the liposome is investigated by looking at the fractured and etched surface of a sample. In the electron micrograph image, giant liposomes having 2~3 um diameter render investigation of the interior of liposomes fairly easy. Networks inside the liposomes were seen and these networks consisted of nanofibers 10~30 nm in width.

Figure 4:
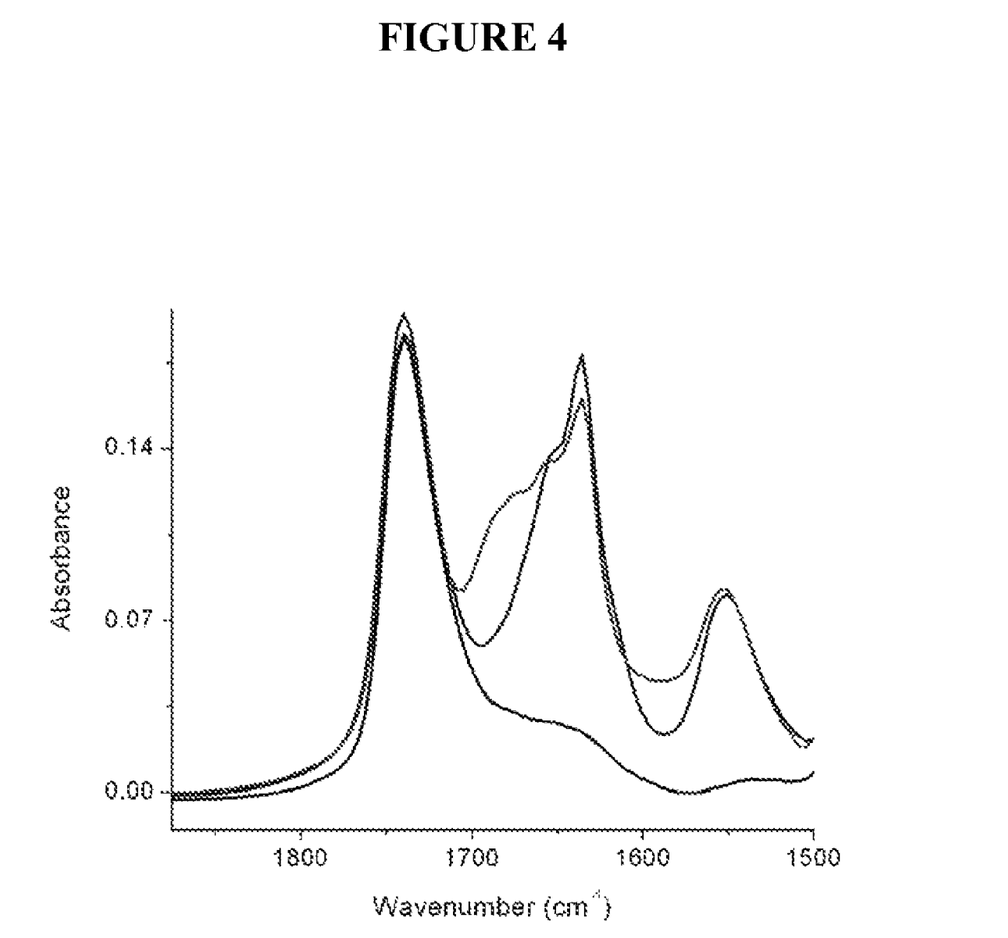
FIG. 4 shows an exemplary FTIR spectra in the amide I region of liposomes alone and liposomes containing PA 1 and PAG before and after irradiation at 254 nm for 1 min

To confirm the nanostructure of aggregates inside a liposome, Fourier transform infrared analysis (FTIR) and circular dichroism (CD) spectroscopic studies were carried out. Upon nanofiber formation, PAs show a characteristic amide stretching peak at 1630 cm$^{-1}$, which corresponds to a β-sheet secondary structure (Niece et al., 2003). Consistent with triggered β-sheet formation, liposomes containing PA 1 and PAG show the stretching peak at 1631 cm$^{-1}$ only after irradiation at 254 nm, which does not appear before irradiation. For the liposomes containing PA 1 and PAG, this band became stronger after irradiation (FIG. 4). The presence of a random coil conformation of the PA also decreased, as evidenced by the reduction of a shoulder at 1665 cm$^{-1}$ (Martinez, et al., 1995, J. Struct. Biol. 114:23). This result is consistent with increased β-sheet character, implying greater PA self-assembly inside the liposomes after irradiation with PAG.

Figure 6:
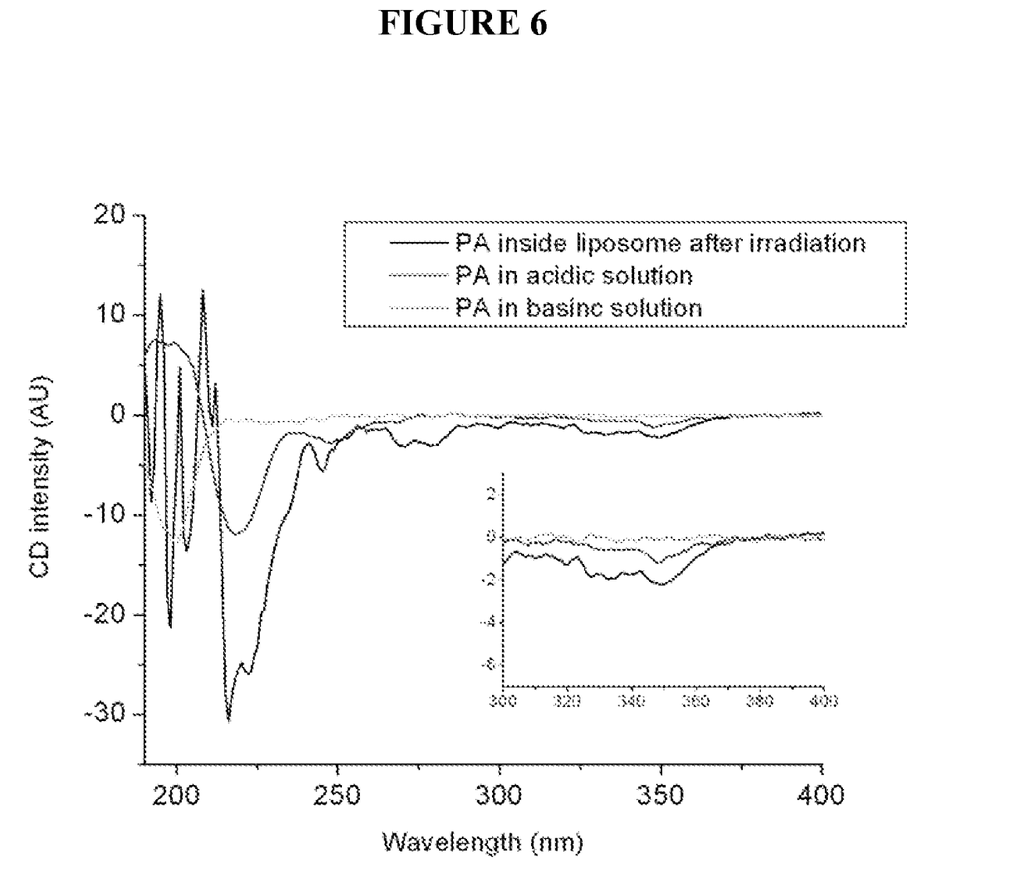
FIG. 6 shows an exemplary CD spectra of PA 3 solution treated with 1 M NaOH (top line), 3 treated with 1 M HCl (middle line) and liposome containing PA 3 and PAG after irradiation (bottom line).

The FTIR data demonstrates that the PA is able to assemble into nanofibers inside the liposome upon irradiation. To further examine PA nanofiber formation inside liposomes, PA 3 reveals the presence of peptide segments in random coil conformation, as indicated by a minimum in the CD-signal at a wavelength of 200 nm (FIG. 6). However, there is a dramatic change showing β-sheet conformation of peptide segment with a minimum in CD signal at 218 nm in acidic solution as well as negative CD signal at around 350 nm that comes from chiral arrangement of pyrene attached to PA 3. This chiral arrangement is also observed after irradiation of a liposome sample encapsulating PA 3 (Guler et al., 2005, J. Mater. Chem. 15:4507). The present invention is not limited to a particular mechanism. Indeed, an understanding of the mechanism is not necessary to practice the present invention. Nonetheless, it is contemplated that the aggregate shown in EM images (FIG. 2) comes from the PA fiber aggregates. The amount of PA encapsulated by liposome is determined based on the measurement of UV absorbance of pyrene attached to PA 3. It was found that ~30% of PA 3 compared to the amount of starting PA can be encapsulated into liposomes.

Figure 3:
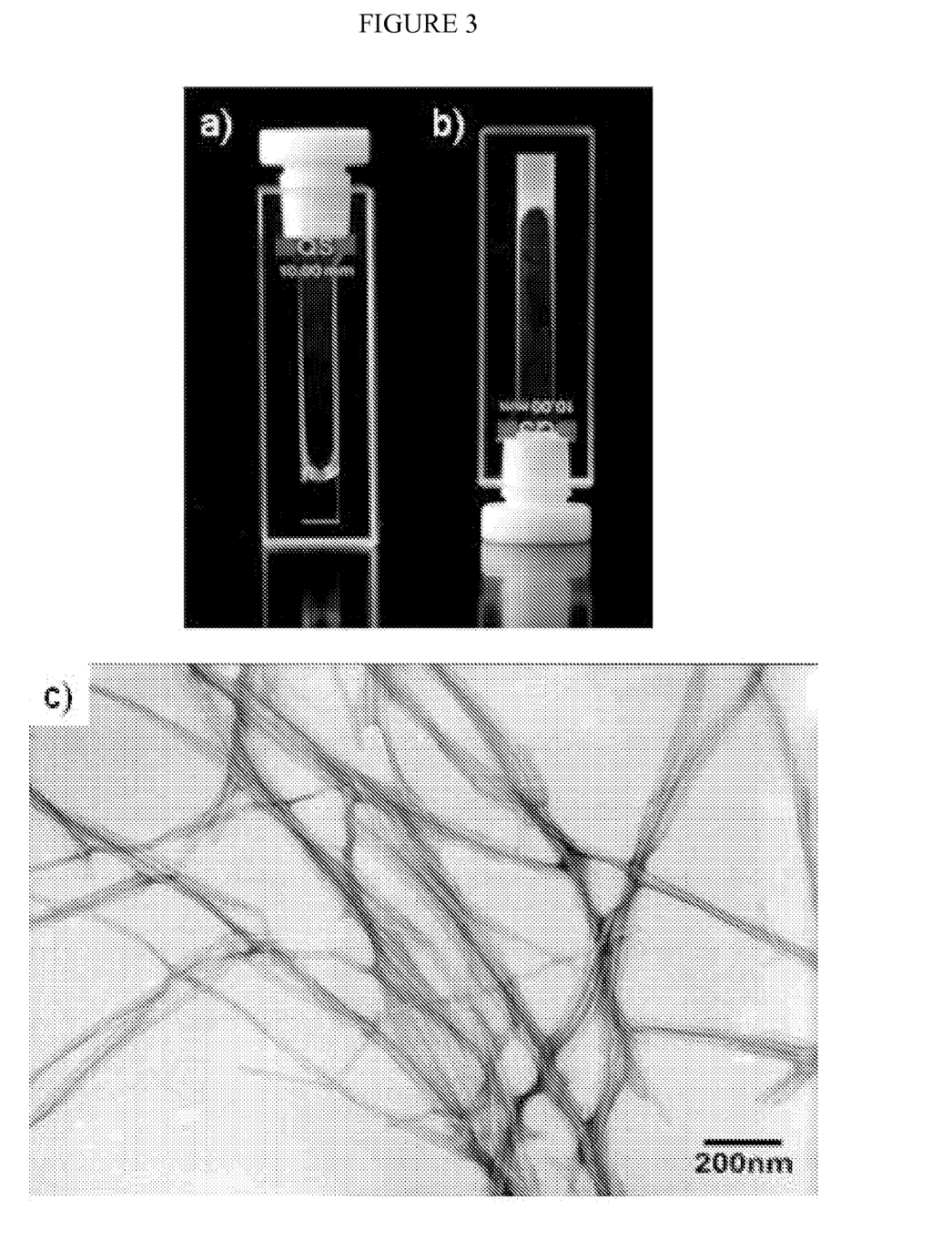
FIG. 3 shows a) 10 mg mL$^{-1}$ of PA 1 with 6 equivalents PAG before irradiation and b) after irradiation at 254 nm. c) TEM image of nanofibers obtained from PA 1 gelled by irradiation in the presence of PAG.

The present invention is not limited by the manner in which the pH is altered. The present invention is also not limited by the identity of the photoacid generators (PAGs) or photobase generators (PBGs) used, when such are used to alter pH. Such photoacid generators are known in the art and include, but are not limited to, iodium salts, sulfonium salts such as benzyldimethylsulfonium chloride, and oxime sulfonates. Further, photobase generators are known in the art and include, but are not limited to, quaternary ammonium salts (e.g., 1-phenacyl-(1-azania-4-azabicyclo[2,2,2,]octane) salts), N,N-dialkyl-substituted O-carbamoyloximes and nitroveratryl protected PEGamines. In addition to the PAG, various model PAs designed to self-assemble under acidic conditions were prepared using standard Fmoc solid-phase peptide synthesis. Gelation of PA 1 by 254 nm UV light in the presence of PAG was observed after 1 min of irradiation (FIG. 3a, b). TEM of the gel revealed a network of nanofibers approximately 10 nm in diameter and several microns in length (FIG. 3c).

Self-assembly of PAs can be controlled by pH, electrostatic interaction, and addition of multivalent ions, thereby causing the ionic character of certain amino acid side chains to be screened so that PAs can effectively interact with each other through hydrogen bonding and induced hydrophobic collapse. In some embodiments, when induction by light is desired, negatively charged PAs are used in combination with PAGs, such that upon application of light acidic conditions are created thereby inducing the self-assembly of the nanofibers from the negatively charges PAs. In some embodiments, when positively charged PAs are used, a PBG is used to induce basic conditions, thereby initiating the self-assembly of the nanofibers from the PAs. For example, one class of PA systems that was designed to form nanofibers under acidic conditions is comprised of a palmitic acid covalently linked to a beta-sheet forming peptide sequence such as AAAAGGG, followed by a negatively charged peptide sequence such as EEE. To assemble this class of PAs into the nanofiber structure inside liposomes, a soluble photoacid generator, such as benzyldimethylsulfonium chloride, is introduced inside the liposome with the PA and used to control the pH of the aqueous compartment inside the liposomes. It is contemplated that photolysis of the PAG by UV irradiation generates a radical cation, which reacts with solvent to give a protic acid, providing a minimally invasive method for decreasing the pH inside the liposome.

Encapsulation of the PA in the aqueous interior of the liposomes may be achieved by known methods. For example, the liposomes may be formed prior to contact with the PAs or they may be made from liposome-forming phospholipids in the presence of PAs. For example, encapsulation may be achieved by using an aqueous solution containing PA and PAG or PBG to hydrate a film comprised of phospholipids, such as asolectin, formed by evaporation from an organic solution. After liposome formation, unencapsulated PA and PAG or PBG are removed by size exclusion chromatography or dialysis. Irradiation of the final mixture lowers the pH (e.g., in the case of PAGs) or increases the pH (e.g., in the case of PBGs) inside the liposomes and triggers assembly of the PA monomers into a nanofiber structure.

It is contemplated that the high density of epitope signals in PA systems can be used to present apoptotic signals to malignant cells, such as cancer cells. For example, the exterior of the liposome is labeled with targeting moieties, such as antibodies to malignant cells, and the interior compartment houses the nanofibers bearing apoptotic sequences. It is contemplated that targeted binding and endocytosis of the liposomes into targeted cells will unleash the bundles and networks of nanofibers inside the cell. Through co-assembly of different PAs, the present invention also provides nanofibers that can combine apoptotic peptides with delivery of therapeutic compounds that are either conjugated to the self-assembling PA monomers or simply encapsulated by the nanofibers inside the liposome.

In one embodiment, the present application provides for a new method to trigger self-assembly of PA nanostructures using photoacid or photobase generators. This makes it possible to self-assemble PA nanofibers inside liposomes by changing pH upon irradiation. In some embodiments, if the PA is negatively charged a photoacid generator is used, whereas if the PA is positively charged a photobase generator is used. It is contemplated that this method is useful for the preparation of highly condensed therapeutic nanofiber bundles in the liposome interior.

In another embodiment, the present invention provides for triggering self-assembly of PA nanostructures within liposomes by introducing multivalent ions in the liposome itself. For example, the introduction of potassium, calcium, manganese, cadmium, zinc, aluminum, and iron ions can be effective in inducing the self-assembly of nanofiber bundles in the liposome interior. The use of such ions is found in United States Patent Publication No. 2004/0001893, herein incorporated by reference in its entirety.

In one embodiment, the present invention provides for the integration of peptide amphiphiles containing, for example, apoptotic sequences for cancer therapy by combining targeted delivery using antibody-tagged liposomes. Several apoptotic sequences are known in the art and include, but are not limited to, KLAKLAKKLAKLAK, Smac/DIABLO peptide (KQAIPVA), and Bid peptide (EDIIRNIARHLAQVGDSMDR). However, the present invention is not limited to cancer therapy. It is contemplated that the present invention is amenable to treating a wide range of diseases where targeted delivery is desirable, for example autoimmune diseases, inflammatory diseases, genetic diseases, degenerative diseases, etc. Those skilled in the art will recognize the possible applications of targeted gene therapy and delivery of compounds to treat diseases by using the methods and compositions of the present invention. Examples of peptide amphiphiles and their uses are described in United States Patent Publication Nos. 2004/0001893 and 2004/0018961, herein incorporated by reference in their entireties. In some embodiments, methods and compositions of the present invention also find use for diagnostic and research applications (e.g., drug screening). For example, a candidate peptide amphiphile may be exposed to a cell or tissue in vitro or in vivo using liposomal delivery to determine the amphilphile's properties (e.g., therapeutic effect, stability, bioavailability, etc.).

In one embodiment, the present invention provides for methods and compositions for modulating diseases. In some embodiments, the methods are useful for treating subjects with cancer. In some embodiments, the present invention provides for the targeting of agents for cancer therapy. In some embodiments, compositions of the present invention comprise apoptotic sequences associated with liposome encapsulated peptide amphiphile nanostructures. In some embodiments, the compositions are administered in vivo to a subject such that the target disease, for example cancer, is modulated. In some embodiments, the compositions of the present invention are co-administered with existing therapies for disease treatment. In some embodiments, the compositions provide targeting signals such that the signals recognize cells associated with specific antigenic sequences for binding purposes. In some embodiments, the antigenic sequences are cancer related. In some embodiments, the antigenic sequences are related to, for example, inflammatory diseases, degenerative diseases, autoimmune diseases. In some embodiments, the present invention provides for a mechanism for delivery of drugs, compounds, small molecules, nucleic acid and amino acid sequences to cells in vivo to a subject and in vitro.

The present invention further provides a kit, comprising a container, reagents and/or other components (e.g., buffers, instructions, solid surfaces, containers, software, etc.) sufficient for, necessary for, or useful for making the compositions of the present invention and/or for practicing the methods of the present invention. A container of a kit includes, but is not limited to, a box, bag, etc. that is provided a user that includes reagents and/or components for making the compositions of the present invention and/or for practicing the methods of the present invention. For example, in some embodiments a kit of the present invention comprises a box that is provided to the user that comprises liposomes, peptide amphiphiles, photo-generators, and for example, additional buffers and reagents for making liposome encapsulated peptide amphiphiles. In some embodiments, the kits would also include instructions for making the compositions of the present invention. In some embodiments, further instructions may include how to use the created compositions in vitro (e.g., in cell culture) or in vivo in a subject. A skilled artisan would understand the different permutations a kit of the present invention would comprise, including different storage conditions required for different components found in a kit of the present invention (e.g., storage conditions such as temperature and light requirements that differ between the different components in the kit).

In some embodiments, the present invention provides pharmaceutically acceptable compositions for use in vivo in a subject. One of skill in the art will appreciate that any one or more of the compounds described herein, including the many specific embodiments, are prepared by applying standard pharmaceutical manufacturing procedures. Such compositions can be delivered to the subject by using delivery methods that are well-known in the pharmaceutical arts. For a more detailed description of therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002, incorporated herein in its entirety.

In some embodiments of the present invention, the compositions are administered alone, while in some other embodiments, the compositions are preferably present in a pharmaceutical formulation comprising at least one active ingredient/agent, as defined above, together with one or more pharmaceutically acceptable carriers, adjuvants and optionally other therapeutic agents. Each carrier should be "acceptable" in the sense that it is compatible with the other ingredients of the formulation and not injurious to the subject.

Contemplated formulations include, for example, oral administration, parenteral administration (e.g., subcutaneous, intramuscular, intravenous, intradermal) and site specific administration. In some embodiments, formulations are conveniently presented in unit dosage form and are prepared by any method known in the art of pharmacy. Such methods include the step of bringing into association the active ingredient with the carrier that constitutes one or more accessory ingredients. In general, the formulations are prepared by uniformly and intimately bringing into association (e.g., mixing) the active ingredient with liquid carriers or finely divided solid carriers or both, and then if necessary shaping the product.

In some embodiments, in vivo administration of the compositions as described herein is effected in one dose, continuously or intermittently throughout the course of treatment. Methods of determining the most effective means and dosage of administration are well known to those of skill in the art and vary with, for example, the composition used for therapy, the target cell being treated and the subject being treated. Single or multiple administrations are carried out with the dose level and pattern being selected by the treating physician.

The present invention also includes methods involving co-administration of the compositions described herein with one or more additional active agents and/or adjuvants. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when treating cancer, the additional agent is a chemotherapeutic agent, anti-cancer agent, or radiation. Treating anti-inflammatory diseases may include the co-administration of compositions of the present invention with, for example, cox-2 inhibitors and/or other non-steroidal anti-inflammatory compositions and/or steroidal anti-inflammatory compositions known in the art.

In some embodiments, the present invention provides methods for using the compositions as described herein for screening for the efficacy of such compositions in inhibiting or decreasing, for example, apoptosis of cells and tissues when such cells and tissues are administered cancer, or other, therapies that are toxic to normal cells. In some embodiments, methods for screening are conducted in in vitro systems. In other embodiments, these screens are conducted in in vivo systems. In some embodiments, methods of the present invention are performed in vivo in animal subjects and/or in vitro in cell lysates, cell and/or tissue explants, cellular extracts, or non-biological based assay systems.

Experimental

The following examples are provided in order to demonstrate and further illustrate certain preferred embodiments and aspects of the present invention and are not to be construed as limiting the scope thereof.

EXAMPLES

Example 1

Peptide Amphiphile Synthesis

Peptide amphiphiles were prepared by standard Fmoc solid-phase synthesis of peptide using a preloaded Wang resin followed by alkylation of the N-terminus with palmitic acid using 2-(1H-benzotriazole-1-yl)-1,1,3,3-tetramethyluronium hexafluorophosphate (HBTU) as the coupling reagent. Cleavage and deprotection of the PA was carried out with a mixture of 95% trifluoroacetic acid (TFA), 2.5% water, and 2.5% triisopropylsilane (TIS).

For PA 2, a Wang resin pre-loaded with Fmoc-Lys(Mtt)-OH was subjected to a 3% solution of TFA in dichloromethane (DCM) with 5% TIS to selectively remove the Mtt protecting group. Palmitic acid was then used to alkylate the lysine side chain amine as described above. Before the cleavage step, the resin was incubated with 6 equivalents fluorescein isothiocyanate (FITC, Sigma) in N,N-dimethylformamide (DMF) with 4 equiv N,N-diisopropylethylamine (DIEA), thereby labeling the PA at the N-terminus of the peptide. PA 3 was synthesized by inserting an Fmoc-Lys(Mtt)-OH into the sequence and selectively removing the Mtt protecting group before coupling of the lysine side chain with pyrene butyric acid (Sigma) using HBTU as the coupling reagent.

Purification of PAs was achieved by preparative HPLC and was performed on a Varian chromatograph using an X-bridge C-18 column in an elution gradient of water (0.1% NH$_4$OH) and acetonitrile (0.1% NH$_4$OH). Purities greater than 95% were obtained after HPLC purification.

Example 2

Liposome Preparation

Liposomes were prepared by the freeze-thaw technique as described by Szoka, 1980, Rev. Biophys. Bioeng. 9:467. Briefly, asolectin (25 mg) from Fluka or a mixture of 1,2-dipalmitoyl-sn-glycero-3-phosphocholine (DPPC); 1,2-dioleoyl-sn-glycero-3-[phospho-rac-(1-glycerol)] (DOPG); and cholesterol (65:5:30) from Avanti Polar Lipids was dissolved in chloroform (2 mL) and concentrated by rotary evaporation to obtain a thin lipid film. The lipids were resuspended in 0.1 M NaOH aqueous media containing PA with PAG by vortexing. The resulting mixture was rapidly frozen in liquid nitrogen then thawed by heating at 45° C. The freeze-thaw procedure was carried out five times successively. Unencapsulated PA molecules and PAG were removed by size exclusion chromatography (Sephadex G-50) or dialysis (10,000 MWCO) over two days.

Example 3

Sample Preparation for Imaging

Samples were prepared using a quick-freeze/deep-etch procedure (Ruberti et al., 2003, Invest. Ophth. Vis. Sci. 44:1753). Each sample was placed on an aluminum tab and slammed onto a copper block cooled to −195° C. by liquid nitrogen (Reichert MM80E). The frozen sample was transferred to a freeze-fracture apparatus (Model 308R; Cressington Scientific Instruments, Watford, UK), in which it was fractured, etched for 25 minutes at −95° C., and rotary shadowed at an angle of 25° with a mixture of platinum and carbon. To strengthen the resulting replica, carbon was evaporated from above the sample, normal to the fractured surface. The coated sample was subsequently submerged in a bleach solution to isolate the platinum-carbon replica. The bleach-cleaned replica films were placed on copper mesh grids for imaging. SEM was performed on a LEO Gemini 1525 microscope.

Example 4

Fourier Transform Infrared (FTIR) Analysis

Samples were prepared as KBr pellets for FTIR analysis. Spectra were obtained using a Thermo Nicolet Nexus 870 spectrometer.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for creating liposome encapsulated peptide amphiphiles comprising:
   a) providing liposomes,
   b) providing peptide amphiphiles,
   c) providing a photoacid generator or a photobase generator,
   d) contacting said liposomes with said peptide amphiphiles and said photoacid generator or photobase generator, wherein said contacting results in encapsulation of said peptide amphiphiles and said photoacid generator or photobase generator within said liposomes, e) triggering the self-assembly of said peptide amphiphiles inside said liposomes upon application of light thereby creating liposome encapsulated peptide amphiphiles.

2. The method of claim 1, wherein said peptide amphiphile is PA 1.

3. The method of claim 1, wherein said peptide amphiphile is PA 2.

4. The method of claim 1, wherein said peptide amphiphile is PA 3.

5. The method of claim 1, wherein said photoacid generator is an iodonium salt, a sulfonium salt, or an oxime sulfonate.

6. The method of claim 5, wherein said photoacid generator is benzyldimethylsulfonium chloride.

7. The method of claim 1, wherein said photobase generator is a quaternary-ammonium-salt, N,N-dialdyl-substituted O-carbamoyloximes, or a nitroveratryl protected PEGamines.

8. A liposome encapsulated peptide amphiphile manufactured by the method of claim 1, wherein said peptide amphiphile is encapsulated within said liposome.

9. A method of creating liposome encapsulated nanofiber structures comprising:
   a) contacting liposome-forming phospholipids with peptide amphiphiles and a photoacid or photobase generator,
   b) inducing the liposome-forming phospholipids to form liposomes containing said peptide amphiphiles and said photoacid or photobase generator, and
   c) triggering the self-assembly of nanofiber structures in the liposomes from said peptide amphiphiles, wherein triggering comprises applying light.

10. The method of claim 9, wherein said photoacid generator is an iodonium salt, a sulfonium salt, or an oxime sulfonate.

11. The method of claim 10, wherein said photoacid generator is benzyldimethylsulfonium chloride.

12. The method of claim 9, wherein said photobase generator is a quaternary-ammonium-salt, N,N-dialdyl-substituted O-carbamoyloximes, or a nitroveratryl protected PEGamines.

13. The method of claim 9, wherein said triggering comprises the introduction of multivalent ions.

14. A method for administering peptide amphiphiles to a subject comprising:
   a) providing liposomes,
   b) providing peptide amphiphiles,
   c) providing a photoacid or a photobase generator,
   d) contacting said liposomes with said peptide amphiphiles and said photoacid or photobase generator,
   e) triggering the self-assembly of said peptide amphiphiles inside said liposomes upon application of light thereby creating liposome encapsulated peptide amphiphiles, and
   f) administering said liposome encapsulated peptide amphiphile to a subject.

15. The method of claim 14, wherein said peptide amphiphile is PA 1.

16. The method of claim 14, wherein said peptide amphiphile is PA 2.

17. The method of claim 14, wherein said peptide amphiphile is PA 3.

18. The method of claim 14, wherein said photoacid generator is benzyldimethylsulfonium chloride.

19. A composition comprising a peptide amphiphile, a liposome and a photoacid generator or a photobase generator, wherein said said peptide amphiphiles and said photoacid generator or photobase generator are encapsulated within said liposome.

20. The composition of claim 19, wherein said amphiphile is PA 1.

21. The composition of claim 19, wherein said peptide amphiphile is PA 2.

22. The composition of claim 19, wherein said peptide amphiphile is PA 3.

23. The composition of claim 19, wherein said photoacid generator is benzyldimethylsulfonium chloride.

* * * * *